United States Patent [19]

Chopin

[11] Plant 4,255

[45] May 30, 1978

[54] CREPE MYRTLE

[75] Inventor: David Earl Chopin, Baton Rouge, La.

[73] Assignee: Chopin & Wright Nursery, Ltd., Baton Rouge, La.

[21] Appl. No.: 781,198

[22] Filed: Apr. 8, 1977

Related U.S. Application Data

[62] Division of Ser. No. 742,378, Nov. 16, 1976, abandoned.

[51] Int. Cl.[2] ..... A01H 5/00

[52] U.S. Cl. ..... Plt./54

[58] Field of Search ..... Plt./54

*Primary Examiner*—Robert E. Bagwill
*Attorney, Agent, or Firm*—Thomas E. Balhoff

[57] ABSTRACT

A new and distinct variety of the Lagerstroemia genus characterized as to novelty by a dwarfness in size, lack of continual vertical growth after maturity and a weeping growth habit at full maturity.

1 Drawing Figure

RELATED APPLICATIONS

This is a division of application Ser. No. 742,378, filed 11-16-76 (and now abandoned).

The present invention relates to a new and distinct variety of ornamental shrub of the species *Lagerstroemia indica,* commonly known as crepe myrtle, characterized as to novelty by its height of 9 to 20 inches or less at full maturity with substantially no vertical growth thereafter as described in the following paragraphs and illustrated in the accompanying color photograph. The new variety has been developed by me during the past 7 years by crossing unnumbered or unnamed seedlings to produce a new ornamental plant which will grow to a height of no more than nine to twenty inches at maturity.

Compact crepe myrtles have been asexually reproduced by others but such plants have been characterized by a continual annual growth after maturity of from 6–8 inches. See U.S. Plant Pat. No. 2,551. Thus, even though these plants are described as dwarf or compact, after several years growth, they will have attained a height far in excess of applicant's plant. The present plant reaches its mature height of 9 to 20 inches or less and does not continue to grow vertically as the plants of the prior art.

The plant has been asexually reproduced in Baton Rouge, La., by means of hardwood and softwood cuttings. All descendants have shown the same characteristics as the original plant, indicating that the new variety is thereby well established. The plant does not produce true from seed.

The plant of the new variety is resistant to freezing and has demonstrated good winter hardiness. The plant has survived temperatures as low as −12° C.

The new variety does not resemble in size or growth habit the original parent plants from which it was derived.

A plant of the new variety is shown in full color in the accompanying photograph. A detailed description of the new variety follows, and to facilitate identification of the important colors, the terminology adapted by the British Horticulture Colour Charts has been followed.

THE PLANT

Parentage: The pollen and seed parents of this plant were unnumbered or unnamed seedlings that had shown desirable characteristics of dwarfness, resulting from previous crosses made by me. The seeds are fertile.

Growth: The plant is comparatively compact, weeping, with its width typically exceeding its height. At maturity, the plant will reach a maximum height of 9 to 20 inches and will grow 6 to 10 inches in height during the first year. There is substantially no vertical growth subsequent to reaching full maturity.

Branches: Multiple branches are freely produced by young seedlings. The branches grow horizontal rather than vertical and are red when immature, turning to brown upon maturity. The mature width is 18 to 22 inches.

Foliage: The leaf arrangement is best described as alternate and are grouped by twos on opposite sides of the stem when mature with a simple type of leaf having a elliptic to ovate shape. Generally, the leaf will have an acute tip, obtuse base, and entire margin. The leaf attachment is stalked, and the leaf venation is pinnate. The leaves will grow in length to 2–4 centimeters and in width to 1–2 centimeters. Finally the leaf will be #144B (Scheele's Green) color.

Flower: The complete flowers will be 2 to 3 centimeters high and have a width of 3 to 4 centimeters, and the flower clusters appear as terminal panicles. There are three to eight florets per flower cluster. The bloom period is early June to October.

Color: The color of the blossom is #75D (Rose-Purple).

I claim:

1. A new distinct variety of *Lagerstroemia indica* plant substantially as shown and described, characterized by the distinctive Rose-Purple color, its height up to 9 to 20 inches, substantially no vertical growth at full maturity, and a weeping growth habit at full maturity.

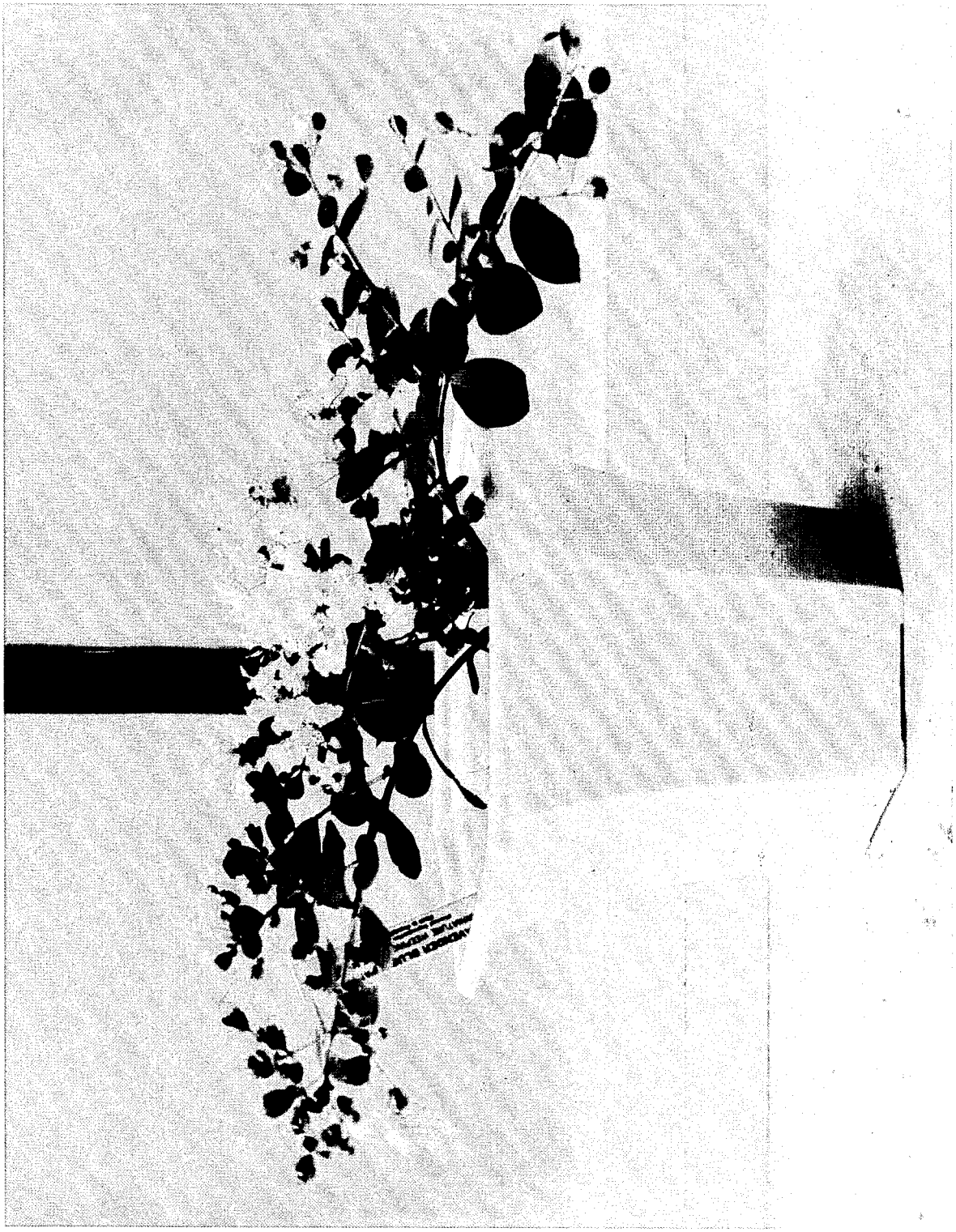

* * * * *